United States Patent
Yokoyama et al.

(10) Patent No.: US 10,059,725 B2
(45) Date of Patent: Aug. 28, 2018

(54) COMPOUND HAVING TRIPHENYLSILYL GROUP AND TRIARYLAMINE STRUCTURE, AND ORGANIC ELECTROLUMINESCENT DEVICE

(75) Inventors: Norimasa Yokoyama, Tasukuba (JP); Shuichi Hayashi, Tsukuba (JP); Yoshio Taniguchi, Ueda (JP); Musubu Ichikawa, Ueda (JP); Shinichi Matsuki, Ueda (JP)

(73) Assignees: Hodogaya Chemical Co., Ltd., Tokyo (JP); Shinshu University, Matsumoto (JP)

( * ) Notice: Subject to any disclaimer, the term of this patent is extended or adjusted under 35 U.S.C. 154(b) by 0 days.

(21) Appl. No.: 12/998,566

(22) PCT Filed: Nov. 9, 2009

(86) PCT No.: PCT/JP2009/005953
§ 371 (c)(1),
(2), (4) Date: May 3, 2011

(87) PCT Pub. No.: WO2010/052932
PCT Pub. Date: May 14, 2010

(65) Prior Publication Data
US 2011/0220881 A1    Sep. 15, 2011

(30) Foreign Application Priority Data
Nov. 7, 2008   (JP) .................. 2008-286479

(51) Int. Cl.
*H01L 51/54* (2006.01)
*C07F 7/10* (2006.01)
(Continued)

(52) U.S. Cl.
CPC .......... *C07F 7/0818* (2013.01); *C07F 7/0812* (2013.01); *C09K 11/06* (2013.01);
(Continued)

(58) Field of Classification Search
None
See application file for complete search history.

(56) References Cited

U.S. PATENT DOCUMENTS

2005/0127823 A1* 6/2005 Iwakuma et al. ............. 313/504
2008/0106188 A1  5/2008 Hwang et al.

FOREIGN PATENT DOCUMENTS

| CN | 101177431 A | 5/2008 |
| JP | 03-235958 A | 10/1991 |

(Continued)

OTHER PUBLICATIONS

Machine English translation of JP 2008-120786 A. Aug. 8, 2012.*
(Continued)

*Primary Examiner* — J. L. Yang
(74) *Attorney, Agent, or Firm* — Locke Lord LLP

(57) ABSTRACT

The invention provides a light emitting layer host compound and an electron-blocking compound that have high excited triplet levels, and can completely confine the triplet excitons of phosphorescent material, for use as the material of a high-efficient organic electroluminescent device. The invention also provides a high-efficient, high-luminance organic electroluminescent device with the use of the compounds.

The compound of the general formula (1) below has a triphenylsilyl group and a triarylamine structure, and the organic electroluminescent device includes a pair of electrodes and at least one organic layer interposed between the pair of electrodes, wherein the compound of the general formula (1) having a triphenylsilyl group and a triarylamine structure is used as constituent material of the at least one organic layer.

(Continued)

← 8 CATHODE
← 7 ELECTRON INJECTION LAYER
← 6 ELECTRON TRANSPORT LAYER
← 5 LIGHT EMITTING LAYER
← 4 ELECTRON BLOCKING LAYER
← 3 HOLE TRANSPORT LAYER
← 2 TRANSPARENT ELECTRODE
← 1 GLASS SUBSTRATE

[Chemical Formula 1]

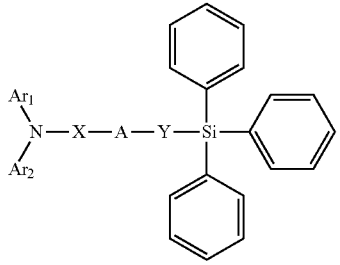

(1)

9 Claims, 1 Drawing Sheet

(51) Int. Cl.
 C07F 7/08 (2006.01)
 C09K 11/06 (2006.01)
 H01L 51/00 (2006.01)
 H01L 51/50 (2006.01)
(52) U.S. Cl.
 CPC ...... *H01L 51/0059* (2013.01); *H01L 51/0094* (2013.01); *C09K 2211/1007* (2013.01); *C09K 2211/1014* (2013.01); *H01L 51/0085* (2013.01); *H01L 51/5012* (2013.01); *H01L 51/5016* (2013.01); *H01L 51/5048* (2013.01); *H01L 51/5096* (2013.01)

(56) References Cited

FOREIGN PATENT DOCUMENTS

| JP | 2001-278889 A | 10/2001 |
| JP | 2004-103463 A | 4/2004 |
| JP | 2006-273791 A | 10/2006 |
| JP | 2008-120786 A | 5/2008 |
| JP | 2008120786 A * | 5/2008 |
| KR | 2007-0106081 A | 11/2007 |
| KR | 2007-0106082 A | 11/2007 |
| WO | WO-2008120899 A1 | 10/2008 |

OTHER PUBLICATIONS

International Search Report dated Dec. 8, 2009, issued for PCT/JP2009/005953.
Office Action, issued for corresponding Chinese Patent Application No. CN2009801044040.0, dated Apr. 2, 2013 (with Japanese translation).
Office Action issued for corresponding Japanese Patent Application No. JP 2010-536703, dated Jan. 21, 2014.
D. Bai et al. "Comparative Study on Tetrahedral and Tripodal Luminescent Silane and Methane Compounds with a 2,2'-Dipyridylamino Group," Organometallics 2004, 23, 5958-5966.
J. Kang et al. "A host material containing tetraphenylsilane for phosphorescent OLEDs with high efficiency and operational stability," Organic Electronics 9 (2008) 452-460.
D. Bai et al. "Charge-Transfer Emission Involving Three-Coordinate Organoboron: V-Shape versus U-Shape and Impact of the Spacer on Dual Emission and Fluorescent Sensing," Chem. Eur. J. 2007, 13, 5713-5723.

* cited by examiner

COMPOUND HAVING TRIPHENYLSILYL GROUP AND TRIARYLAMINE STRUCTURE, AND ORGANIC ELECTROLUMINESCENT DEVICE

TECHNICAL FIELD

The present invention relates to compounds and devices suited for organic electroluminescent devices, a type of self-emitting device suitable for various types of display devices, specifically to compounds having a triphenylsilyl group and a triarylamine structure, and organic electroluminescent devices using the compounds.

BACKGROUND ART

Organic electroluminescent devices are a self-emitting device that provides better brightness and visibility than liquid crystal devices, and thus realize clearer display. For this reason, there have been active studies on organic electroluminescent devices.

In an attempt to improve the luminous efficiency of the devices, devices that phosphoresce with the use of phosphorescent material, specifically that utilize the emission from the triplet excited state have been developed. According to the theory of excitation state, the use of phosphorescent emission realizes luminous efficiency as high as about 4 times that of conventional fluorescence, and a prominent increase can be expected for luminous efficiency.

In 1993, M. A. Baldo and others of Princeton University achieved an 8% external quantum efficiency with a phosphorescent device using an iridium complex.

Because phosphorescent material undergoes concentration quenching, the phosphorescent material is held by being doped in charge-transporting compounds, or host compounds as they are generally called. The phosphorescent material held in this manner is called a guest compound. The 4,4'-di(N-carbazolyl)biphenyl (hereinafter, "CBP") of the following formula has been commonly used as such host compounds (see, for example, Non-Patent Document 1).

[Chemical Formula 1]

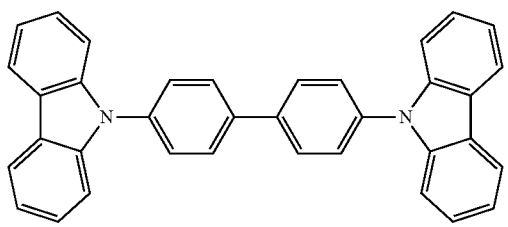

However, because CBP is highly crystalline, the poor stability in the thin-film state has been pointed out. Accordingly, it has not been possible to obtain device characteristics, such as high-luminance emission, that are satisfactory in situations requiring heat resistance.

In this connection, the 4,4',4''-tri(N-carbazolyl)triphenylamine (hereinafter, "TCTA") of the following formula has been proposed as a new host compound, and luminous efficiency comparable to that of CBP has been confirmed (see, for example, Non-Patent Document 2).

[Chemical Formula 2]

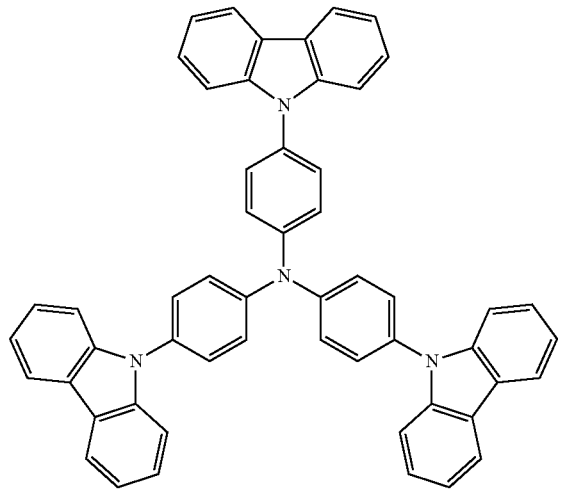

As the studies of phosphorescent device progress, there is an increased level of understanding of the energy transfer process between the phosphorescent material and the host compound. This has made it clear that the excited triplet levels of the host compound need to be higher than the excited triplet levels of the phosphorescent material for improved luminous efficiency. Accordingly, there is a need for a host compound having higher excited triplet levels than CBP. Studies of host compounds having higher excited triplet levels have found that doping an electron-transporting or bipolar-transporting host compound with an iridium complex can yield higher luminous efficiency (see, for example, Non-Patent Document 3).

Further, there is a light emitting layer produced by doping the green phosphorescent material Ir(ppy)3 of the following formula

[Chemical Formula 3]

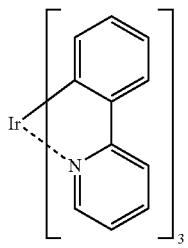

in a mixed host compound that includes the hole-transporting host compound TCTA and the electron-transporting host compound TPBI of the following formula.

[Chemical Formula 4]

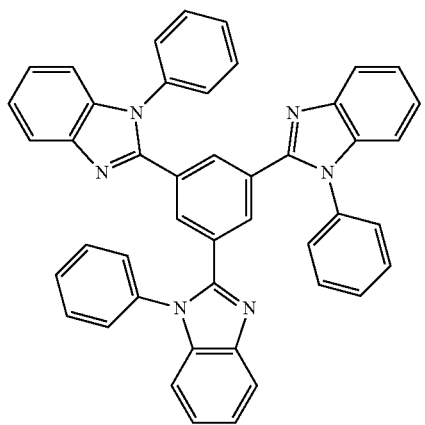

The use of TCTA for the triplet exciton-confining electron blocking layer can achieve high efficiency and low voltage driving (see, for example, Non-Patent Document 4).

On the other hand, the external quantum efficiency of a phosphorescent device in which the CBP doped with the blue phosphorescent material FIrpic of the following formula is used as the host compound of the light emitting layer remains only at 6%.

[Chemical Formula 5]

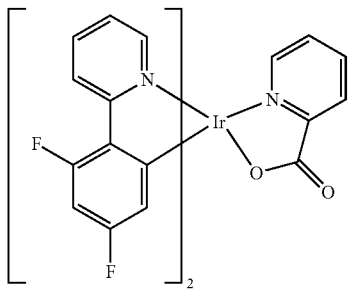

This is considered to be due to the insufficient confinement of the triplet excitons by FIrpic, attributed to the lower excited triplet level 2.56 eV of CBP compared to the excited triplet level 2.62 eV of FIrpic.

This has been demonstrated by the temperature-dependent photoluminescence intensity of a thin film produced by doping CBP with FIrpic (see, for example, Non-Patent Document 5).

Further, the excited triplet level of the TCTA used as the electron blocking layer of the green phosphorescent device is 2.60 eV, a value still considered to be insufficient for the confinement of the FIrpic triplet excitons.

Accordingly, there is a need for a light emitting layer host compound and an electron-blocking compound that can completely confine the triplet excitons of the phosphorescent material, in order to improve the luminous efficiency of the phosphorescent device.

CITATION LIST

Non-Patent Documents

Non-Patent Document 1: Appl. Phys. Lett., 75, 4 (1999)
Non-Patent Document 2: The Japan Society of Applied Physics, Molecular Electronics and Bioelectronics, Ninth Workshop, 17 (2001)
Non-Patent Document 3: Ohmsha, Ltd., Organic EL Display, 90 (2005)
Non-Patent Document 4: SID 07 DIGEST 837 (2007)
Non-Patent Document 5: Journal of The Japan Society of Applied Physics, Molecular Electronics and Bioelectronics, 14(1), 23 (2003)

SUMMARY OF INVENTION

Problems that the Invention is to Solve

An object of the present invention is to provide a light emitting layer host compound and an electron-blocking compound that have high excited triplet levels, and can completely confine the triplet excitons of phosphorescent material, for use as the material of a high-efficient organic electroluminescent device. The invention also provides a high-efficient, high-luminance organic electroluminescent device with the use of the compounds. The physical characteristics of the organic compound provided by the present invention include (1) high excited triplet levels, (2) bipolar transporting property, and (3) stable thin-film state. The physical characteristics desired for the organic electroluminescent device provided by the present invention include (1) high luminous efficiency, (2) high emission luminance, and (3) low actual driving voltage.

Means for Solving the Problems

In order to achieve the foregoing objects, the present inventors looked at the electron transporting capability of a triphenylsilyl group, and the hole transporting capability of a triarylamine structure, and designed and chemically synthesized compounds using the excited triplet level as an index. As a result of actual measurements of excited triplet level, the present inventors found novel compounds having a triphenylsilyl group and a triarylamine structure, and of properties suited for phosphorescent devices. The present invention was completed after dedicated evaluations of device characteristics based on various prototype organic electroluminescent devices produced with the compounds.

Specifically, the present invention is a compound of the general formula (1) below having a triphenylsilyl group and a triarylamine structure and is an organic electroluminescent device which includes a pair of electrodes and at least one organic layer interposed between the pair of electrodes, wherein the compound of the general formula (1) having a triphenylsilyl group and a triarylamine structure is used as constituent material of the at least one organic layer.

[Chemical Formula 6]

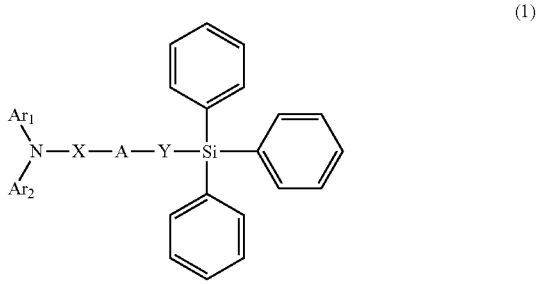

(1)

(wherein X and Y may be the same or different, and represent a substituted or unsubstituted divalent aromatic hydrocarbon group, Ar1 and Ar2 may be the same or different, and represent a substituted or unsubstituted aromatic hydrocarbon group, a substituted or unsubstituted aromatic heterocyclic group, or a substituted or unsubstituted condensed polycyclic aromatic group, which may bind to each other to form a ring structure, and A represents a divalent group of the structural formulae (B) to (H) below, or a single bond)

[Chemical Formula 7]

(B)

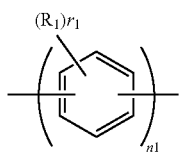

(wherein R1 represents a fluorine atom, a chlorine atom, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group, where a plurality of R1 may be different from each other, r1 is an integer of 0 to 4, and the divalent group (B) is not substituted with R1 when r1 is 0, n1 is an integer of 1 to 2, where a plurality of r1 may be different from each other when n1 is 2)

[Chemical Formula 8]

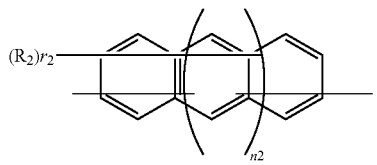

(wherein R2 represents a fluorine atom, a chlorine atom, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group, where a plurality of R2 may be different from each other, n2 represents 0 or 1, r2 is an integer of 0 to 6 when n2 is 0, where the divalent group (C) is not substituted with R2 when r2 is 0, r2 is an integer of 0 to 8 when n2 is 1, where the divalent group (C) is not substituted with R2 when r2 is 0)

[Chemical Formula 9]

(D)

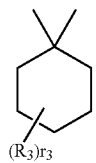

(wherein R3 represents a fluorine atom, a chlorine atom, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group, where a plurality of R3 may be different from each other, r3 is an integer of 0 to 10, where the divalent group (D) is not substituted with R3 when r3 is 0)

[Chemical Formula 10]

(E)

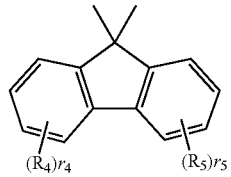

(wherein R4 and R5 may be the same or different, and represent a fluorine atom, a chlorine atom, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group, where a plurality of R4 or R5 may be different from each other, r4 and r5 are integers of 0 to 4, where the divalent group (E) is not substituted with R4 or R5 when r4 or r5 is 0)

[Chemical Formula 11]

(F)

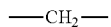

[Chemical Formula 12]

(G)

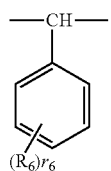

(wherein R6 represents a fluorine atom, a chlorine atom, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group, where a plurality of R6 may be different from each other, r6 is an integer of 0 to 5, where the divalent group (G) is not substituted with R6 when r6 is 0)

[Chemical Formula 13]

(H)

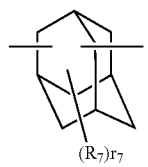

(wherein R7 represents a fluorine atom, a chlorine atom, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group, where a plurality of R7 may be different from each other, r7 is an integer of 0 to 12, where the divalent group (H) is not substituted with R7 when r7 is 0).

Specific examples of the "aromatic hydrocarbon group", "aromatic heterocyclic group", or "condensed polycyclic aromatic group" of the "substituted or unsubstituted aromatic hydrocarbon group", "substituted or unsubstituted aromatic heterocyclic group", or "substituted or unsubstituted condensed polycyclic aromatic group" represented by R1 to R7 and Ar1 to Ar2 in the general formula (1) and the structural formulae (B) to (H) include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a triazyl group, a pyrimidyl group, a furanyl group, a pyronyl group, a thienyl group, a quinolyl group, an isoquinolyl group, a benzofuranyl group, a benzothienyl group, an indolyl group, a carbazolyl group, a benzooxazolyl group, a benzothiazolyl group, a quinoxalyl group, a benzoimidazolyl group, a pyrazolyl group, a dibenzofuranyl group, a dibenzothienyl group, a naphthyridinyl group, a phenanthrolinyl group, and an acridinyl group. Specific examples of the ring structure formed by the binding of Ar1 to Ar2 include a carbazole ring, a pyridoindole ring, a dipyridopyrrole ring, a dipyridoimidazole ring, and a pyrimidobenzimidazole ring.

Specific examples of the "substituent" of the "substituted aromatic hydrocarbon group", "substituted aromatic heterocyclic group", or "substituted condensed polycyclic aromatic group" represented by R1 to R7 and Ar1 to Ar2 in the general formula (1) and structural formulae (B) to (H) include a fluorine atom, a chlorine atom, a trifluoromethyl group, a linear or branched alkyl group of 1 to 6 carbon atoms, a phenyl group, a biphenylyl group, a terphenylyl group, a tetrakisphenyl group, a styryl group, a naphthyl group, a fluorenyl group, a phenanthryl group, an indenyl group, a pyrenyl group, and a disubstituted amino group, and these may be further substituted. The "substituent" of the disubstituted amino group may be, for example, the same "aromatic hydrocarbon group", "aromatic heterocyclic group", or "condensed polycyclic aromatic group" exemplified for R1 to R7 and Ar1 to Ar2.

Specific examples of the "linear or branched alkyl group of 1 to 6 carbon atoms" represented by R1 to R7 in the structural formulae (B) to (H) include a methyl group, an ethyl group, an n-propyl group, an i-propyl group, an n-butyl group, an i-butyl group, a t-butyl group, an n-pentyl group, an i-pentyl group, a t-pentyl group, an n-hexyl group, an i-hexyl group, and a t-hexyl group.

The "linear or branched alkyl group of 1 to 6 carbon atoms" as the "substituent" of the "substituted aromatic hydrocarbon group", "substituted aromatic heterocyclic group", or "substituted condensed polycyclic aromatic group" represented by R1 to R7 and Ar1 to Ar2 in the general formula (1) and structural formulae (B) to (H) may be the same group exemplified above.

Examples of the "substituted or unsubstituted divalent aromatic hydrocarbon group" represented by X and Y in the general formula (1) include divalent groups that result from the removal of two hydrogen atoms from compounds such as benzene, naphthalene, and anthracene. The "substituent" of the "substituted divalent aromatic hydrocarbon group" may be, for example, the same "substituent" exemplified as the substituent of the "substituted aromatic hydrocarbon group", "substituted aromatic heterocyclic group", or "substituted condensed polycyclic aromatic group" for R1 to R7 and Ar1 to Ar2.

The compound of the general formula (1) having a triphenylsilyl group and a triarylamine structure of the present invention is a novel compound, and has higher excited triplet levels than conventional electron blocking layer materials, superior triplet exciton confining capability, and a stable thin-film state.

The compound of the general formula (1) having a triphenylsilyl group and a triarylamine structure of the present invention can be used as the constituent material of the light emitting layer or electron device layer of an organic electroluminescent device (hereinafter, "organic EL device"). The use of the compound of the present invention having a better bipolar transporting property than conventional materials improves luminous efficiency, and lowers the actual driving voltage.

Advantage of the Invention

A compound having a triphenylsilyl group and a triarylamine structure of the present invention is useful as an electron-blocking compound of an organic EL device or a host compound of a light emitting layer. An organic EL device fabricated with the compound has high luminous efficiency, high luminance, and low driving voltage.

MODE FOR CARRYING OUT THE INVENTION

Figure 1:
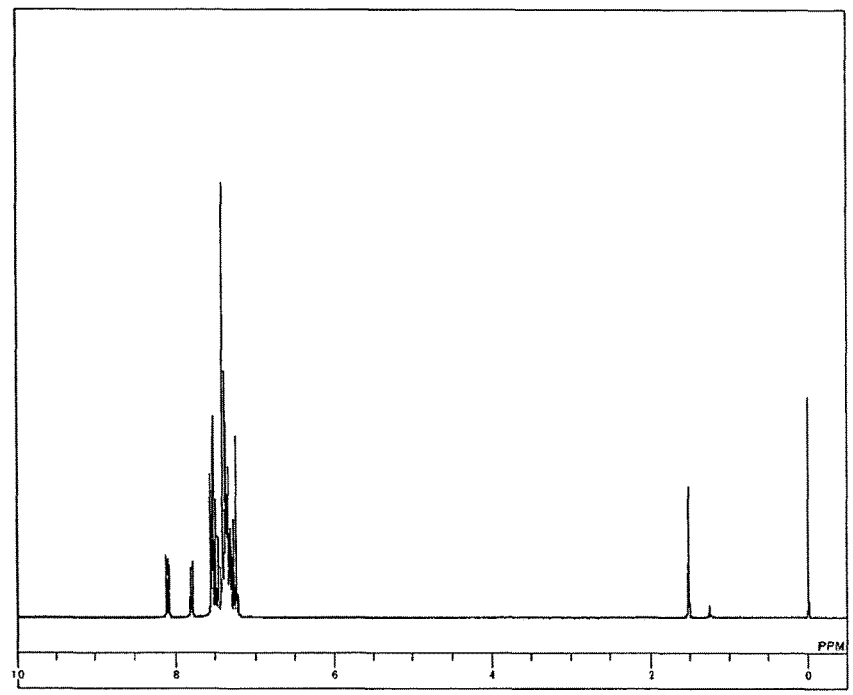
FIG. 1 is a 1H-NMR chart for a compound (Compound 25) of Example 1 of the present invention.

A compound having a triphenylsilyl group and a triarylamine structure of the present invention is a novel compound, and can be synthesized by, for example, the Ullmann reaction of bis(iodophenyl)fluorene and corresponding arylamines, or by the amination reaction with a palladium catalyst to give a corresponding [(arylamino)phenyl]-(iodophenyl)fluorene, which is then allowed to react with triphenylsilylchloride after lithiation with n-butyllithium.

Preferred examples of the compound of general formula (1) having a triphenylsilyl group and a triarylamine structure are specifically presented below. The present invention, however, is not limited to the following compounds.

[Chemical Formula 14]
(Compound 7)
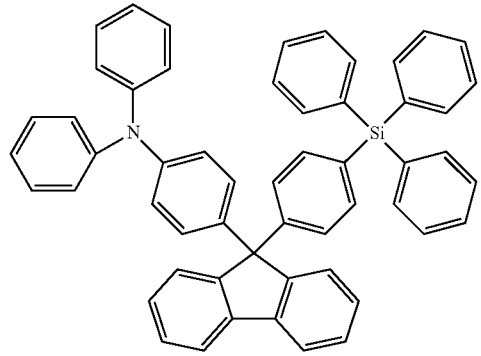
[Chemical Formula 15]
(Compound 8)
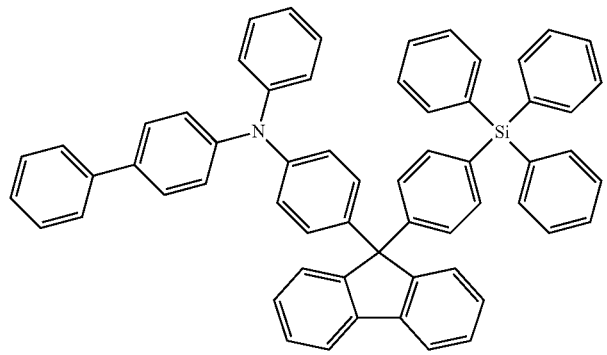
[Chemical Formula 16]
(Compound 9)
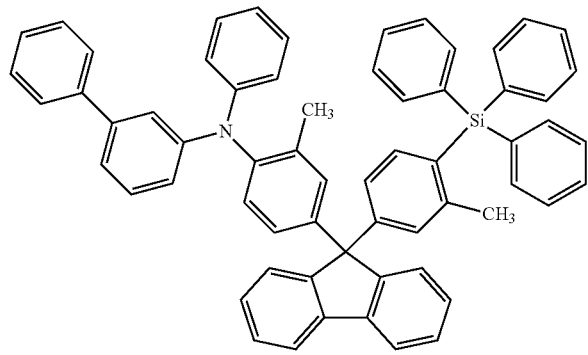
[Chemical Formula 17]
(Compound 10)
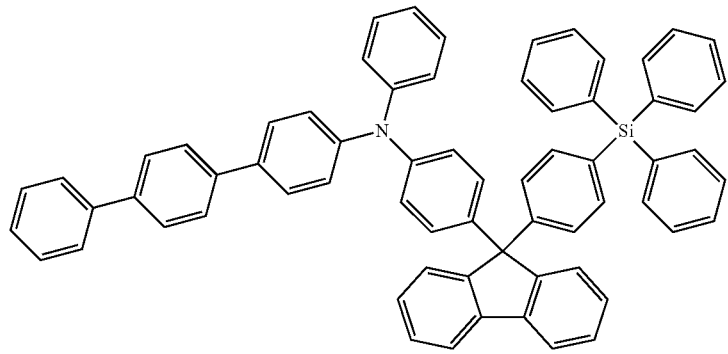

[Chemical Formula 18]
(Compound 11)
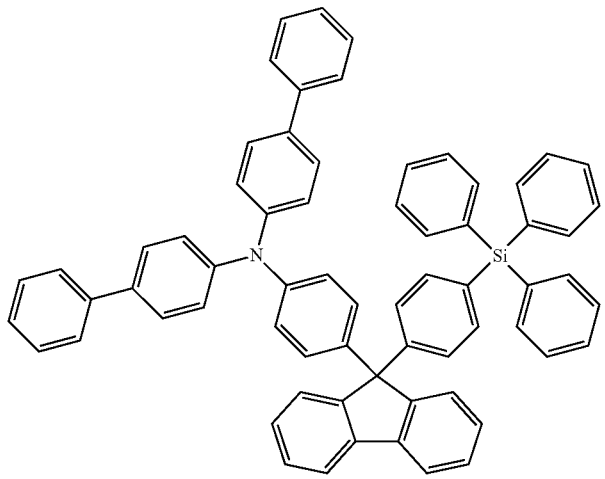
[Chemical Formula 19]
(Compound 12)
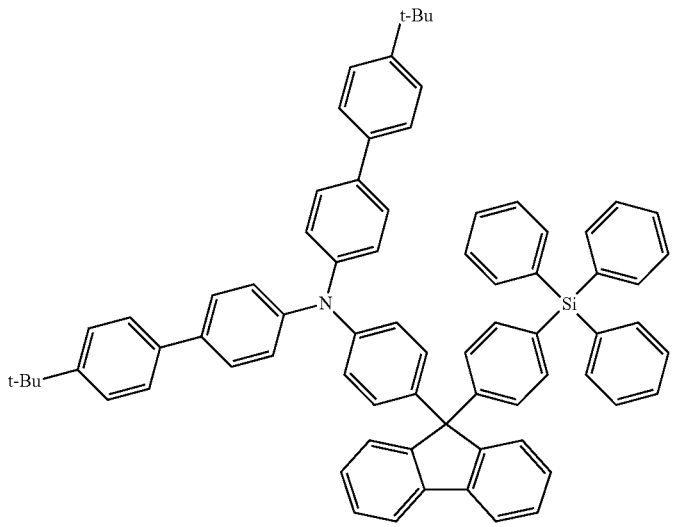
[Chemical Formula 20]
(Compound 13)
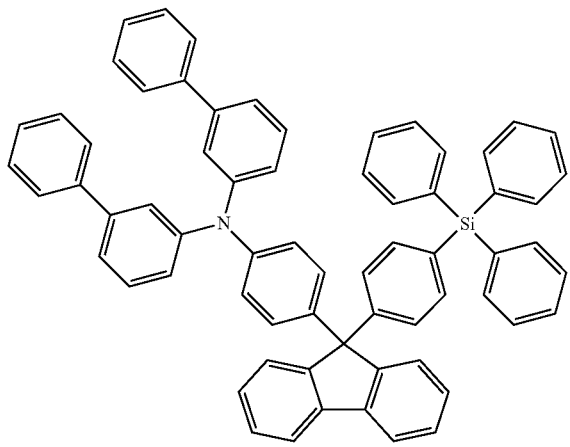

-continued
[Chemical Formula 21] (Compound 14)
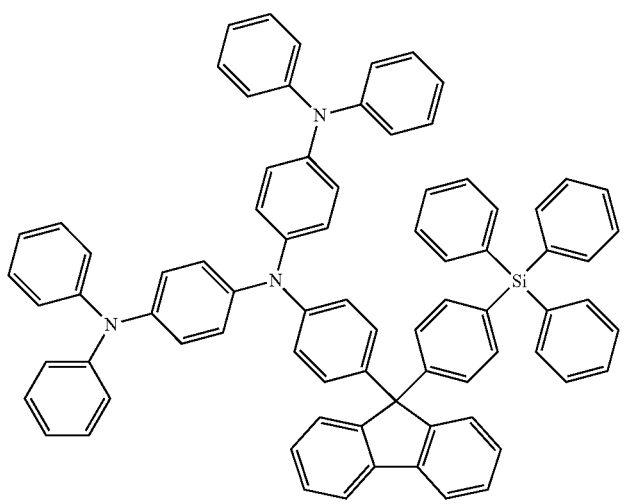
[Chemical Formula 22] (Compound 15)
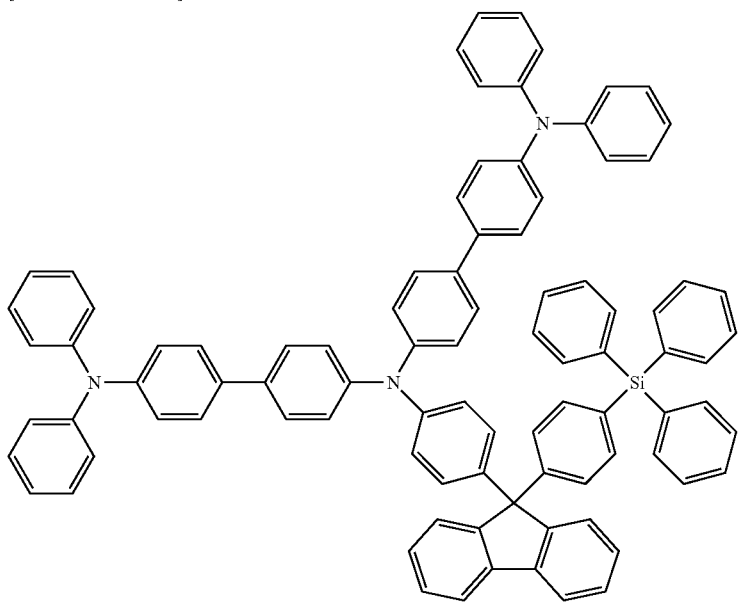
[Chemical Formula 23] (Compound 16)
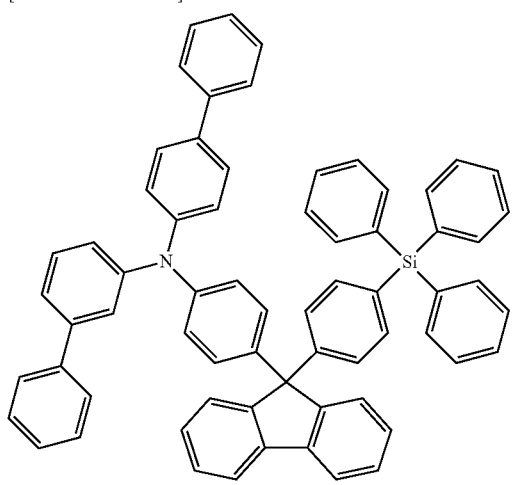

-continued
[Chemical Formula 24]
(Compound 17)
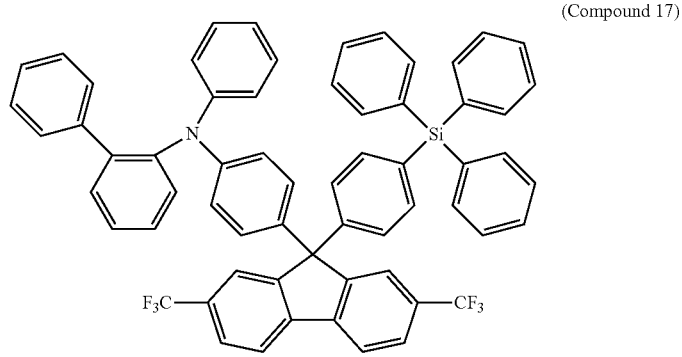
[Chemical Formula 25]
(Compound 18)
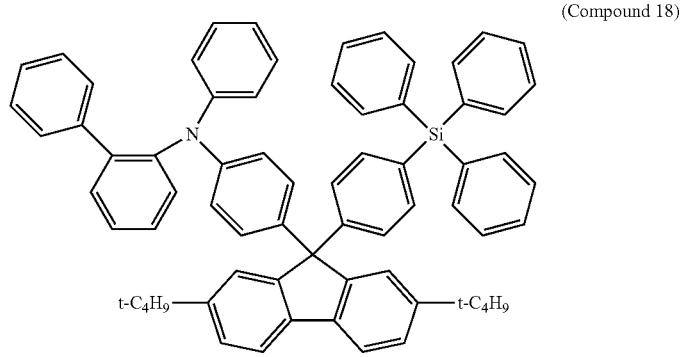
[Chemical Formula 26]
(Compound 19)
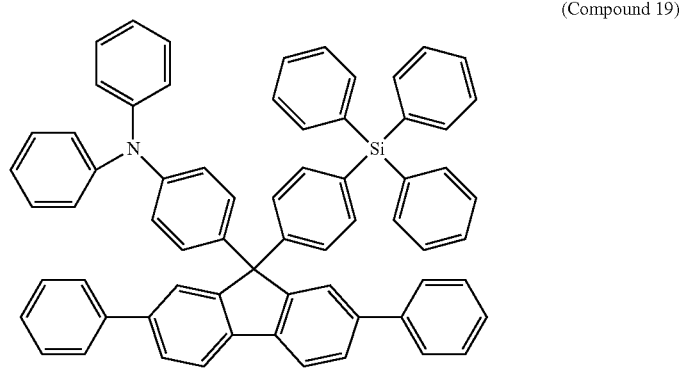
[Chemical Formula 27]
(Compound 20)
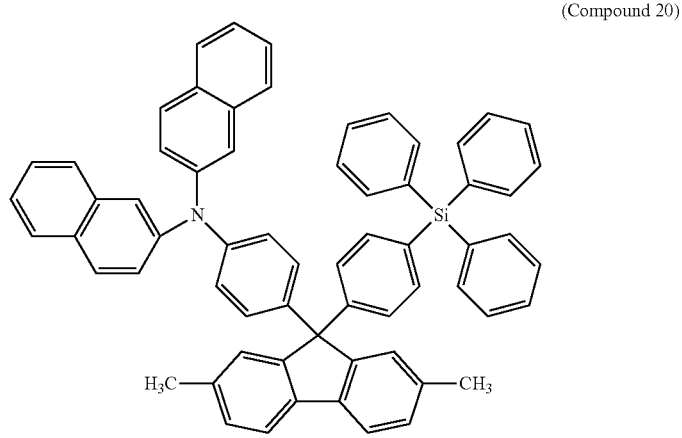

-continued
[Chemical Formula 28]
(Compound 21)
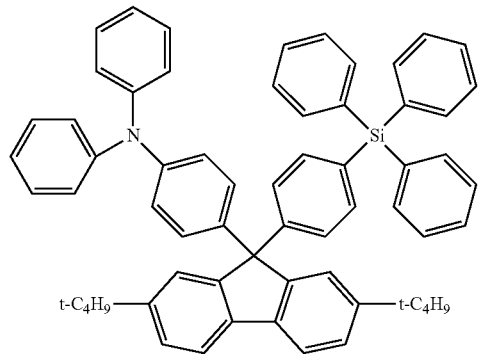
[Chemical Formula 29]
(Compound 22)
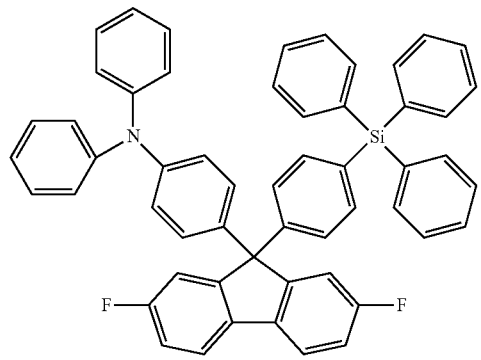
[Chemical Formula 30]
(Compound 23)
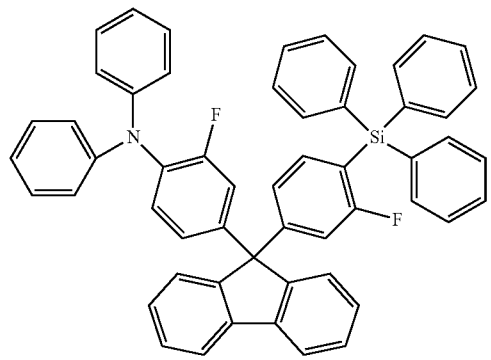
[Chemical Formula 31]
(Compound 24)
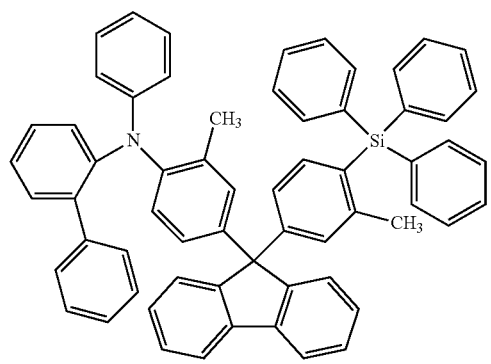

[Chemical Formula 32]
(Compound 25)
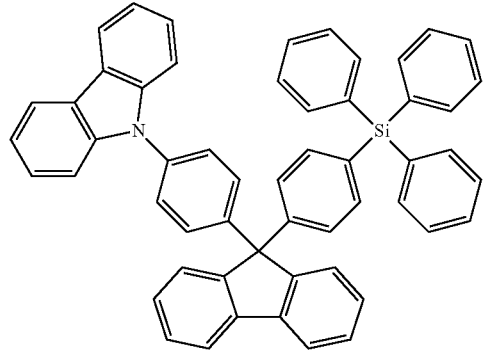
[Chemical Formula 33]
(Compound 26)
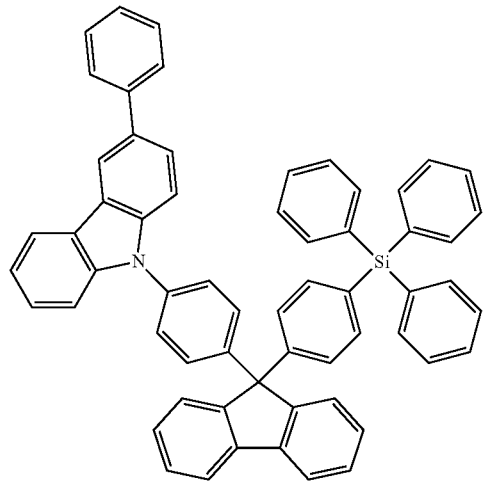
[Chemical Formula 34]
(Compound 27)
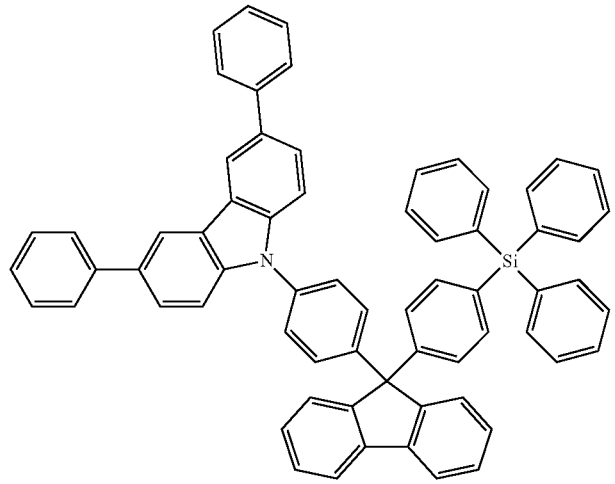

[Chemical Formula 35]
(Compound 28)
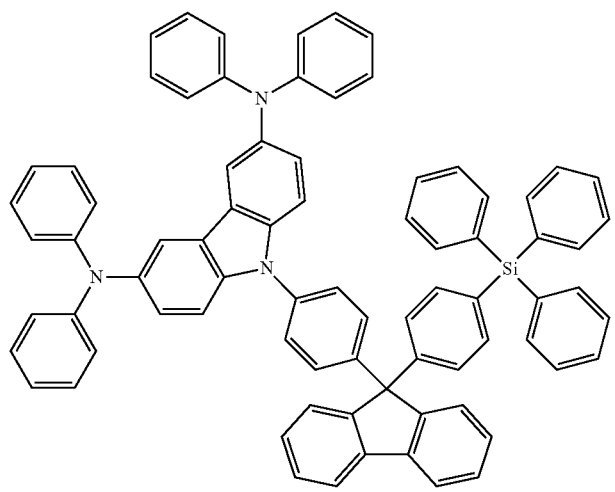
[Chemical Formula 36]
(Compound 29)
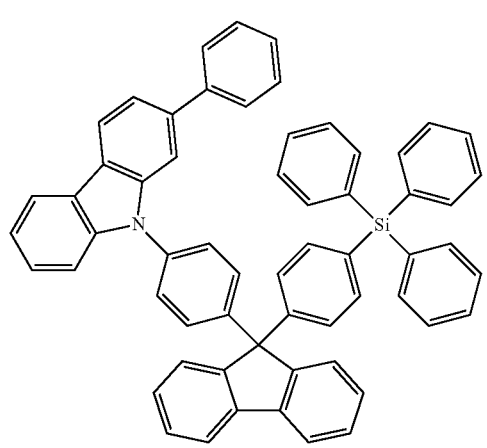
[Chemical Formula 37]
(Compound 30)
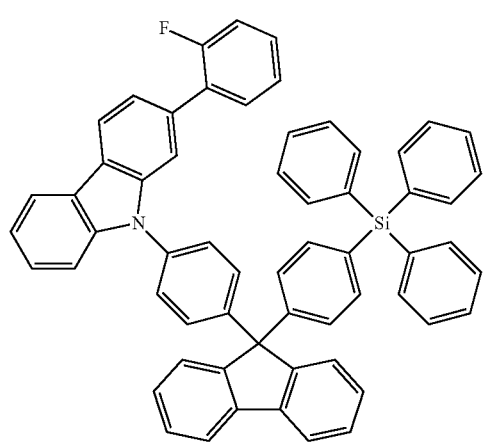

[Chemical Formula 38]
(Compound 31)
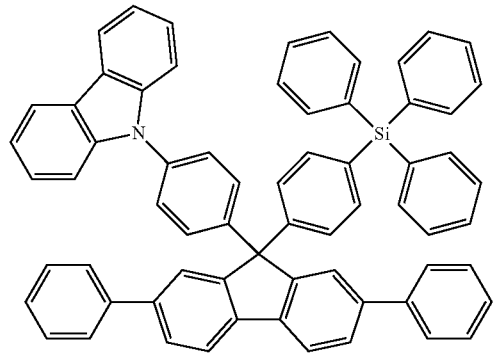
[Chemical Formula 39]
(Compound 32)
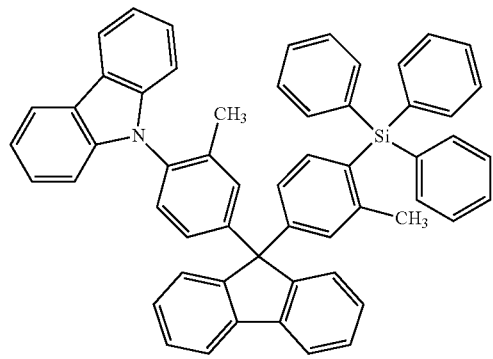
[Chemical Formula 40]
(Compound 33)
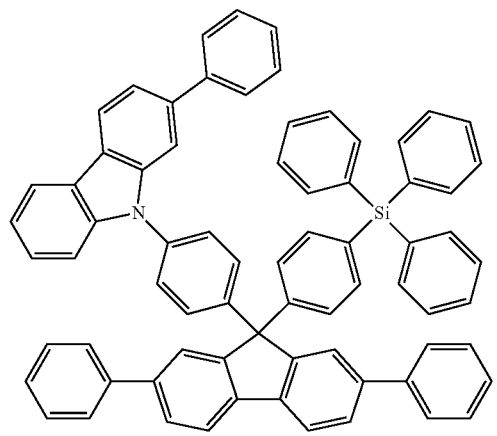

[Chemical Formula 41]
(Compound 34)
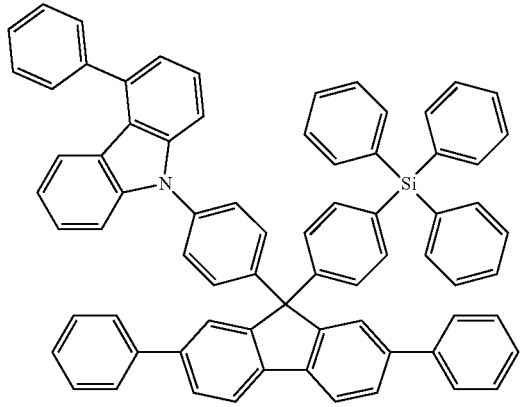
[Chemical Formula 42]
(Compound 35)
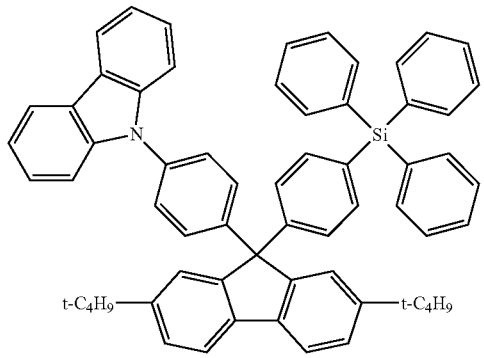
[Chemical Formula 43]
(Compound 36)
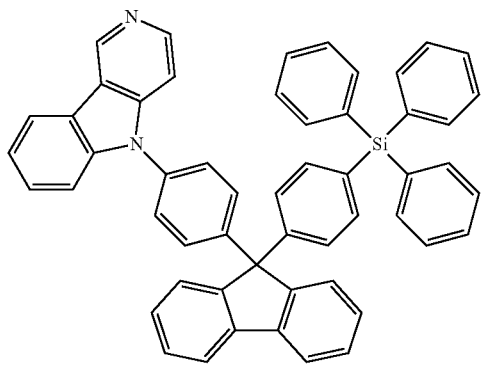

-continued
[Chemical Formula 44]
(Compound 37)
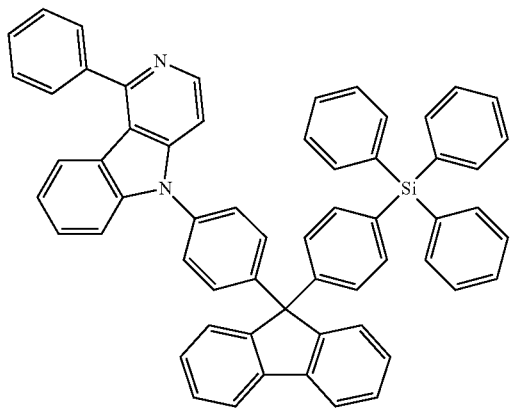
[Chemical Formula 45]
(Compound 38)
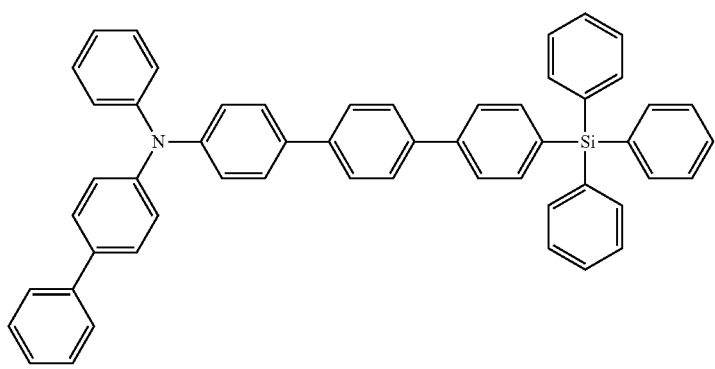
[Chemical Formula 46]
(Compound 39)
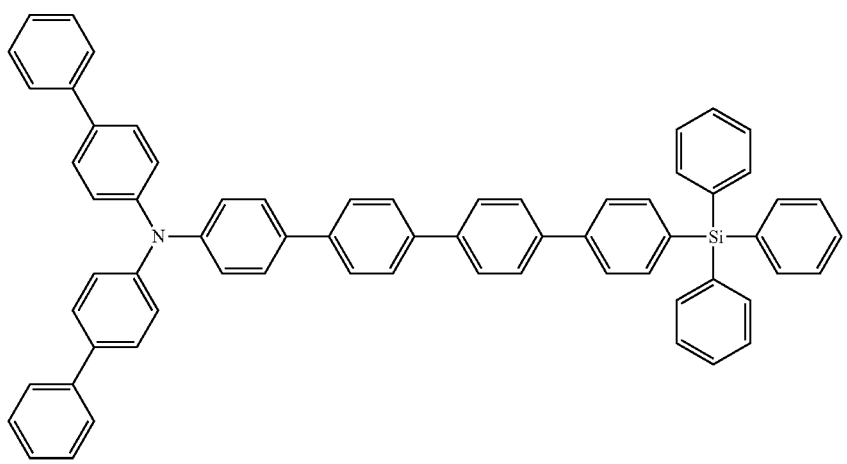
[Chemical Formula 47]
(Compound 40)
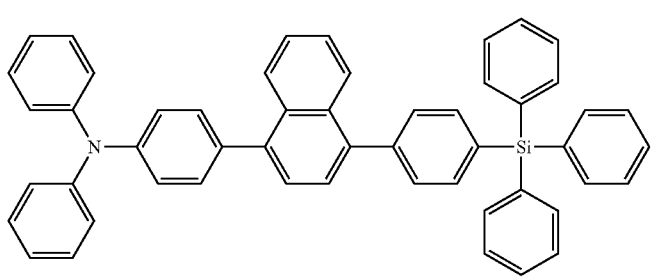

[Chemical Formula 48]
(Compound 41)
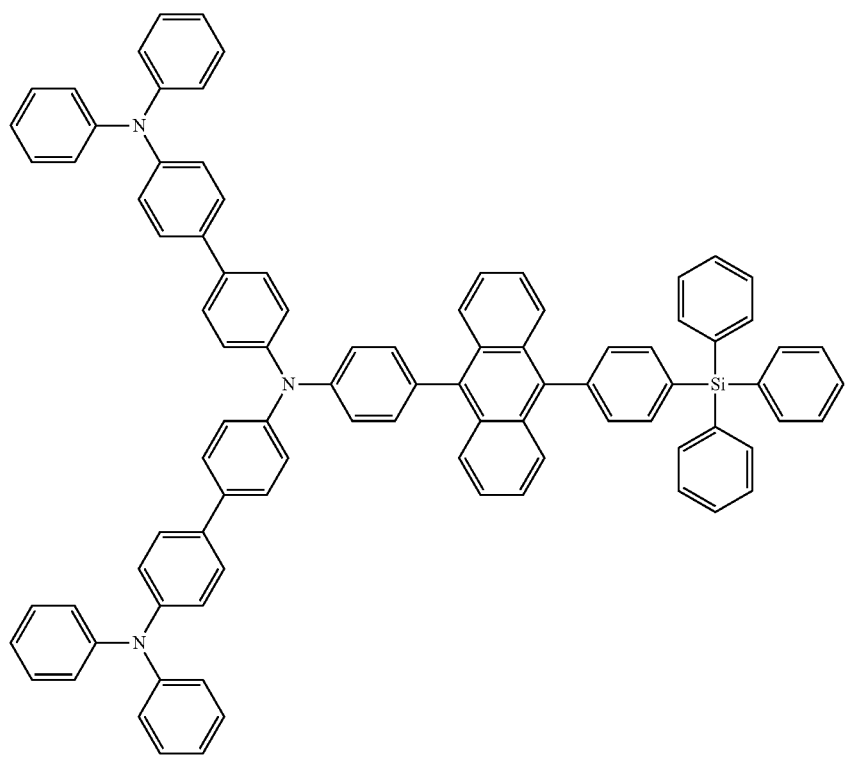
[Chemical Formula 49]
(Compound 42)
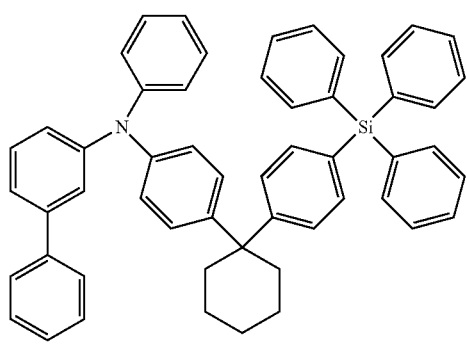
[Chemical Formula 50]
(Compound 43)
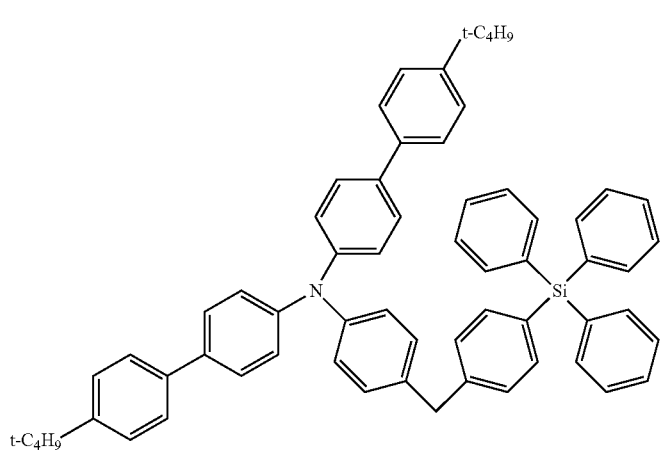

[Chemical Formula 51]
(Compound 44)
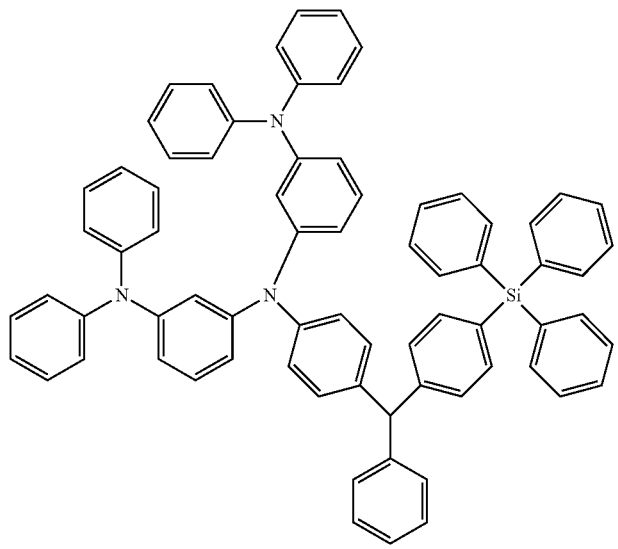
[Chemical Formula 52]
(Compound 45)
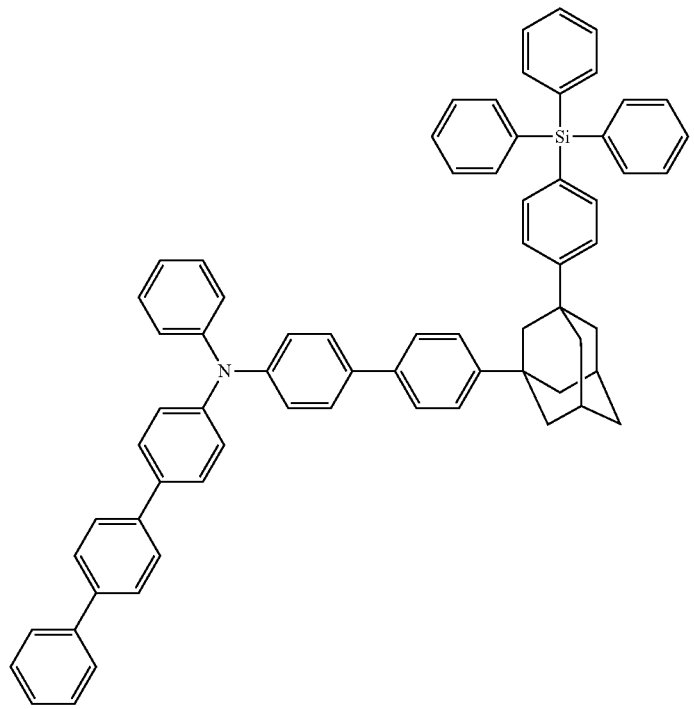

-continued
[Chemical Formula 53]
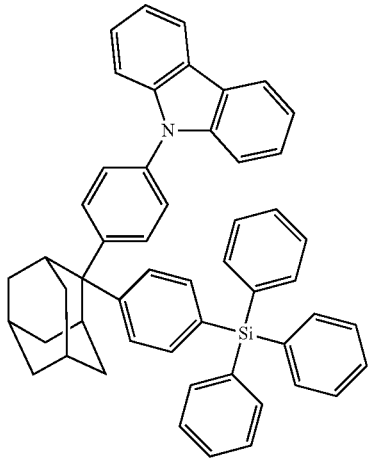
(Compound 46)
[Chemical Formula 54]
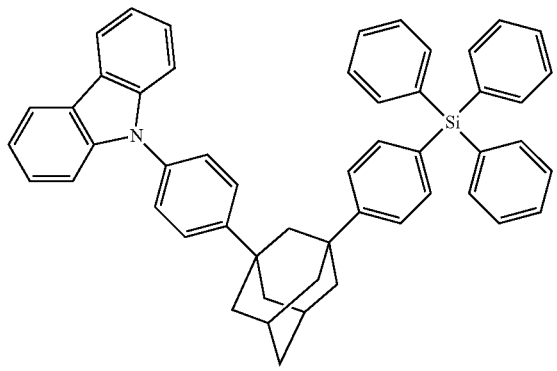
(Compound 47)
[Chemical Formula 55]
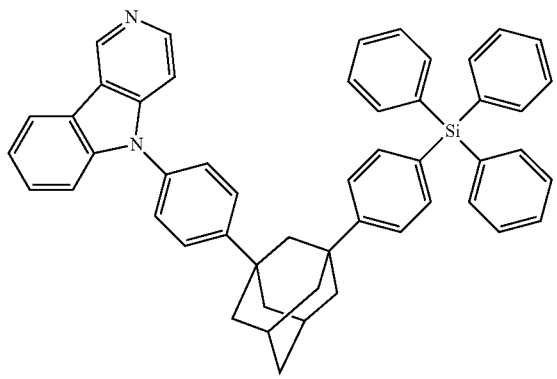
(Compound 48)

-continued

[Chemical Formula 56]

(Compound 49)

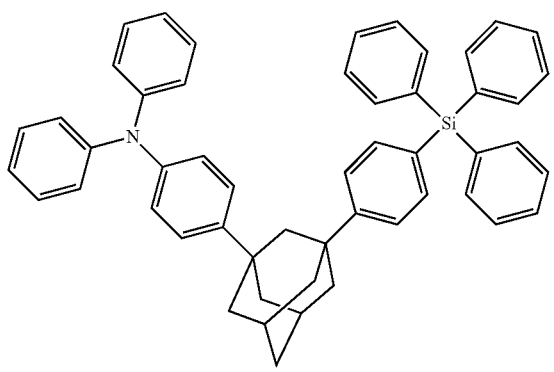

[Chemical Formula 57]

(Compound 50)

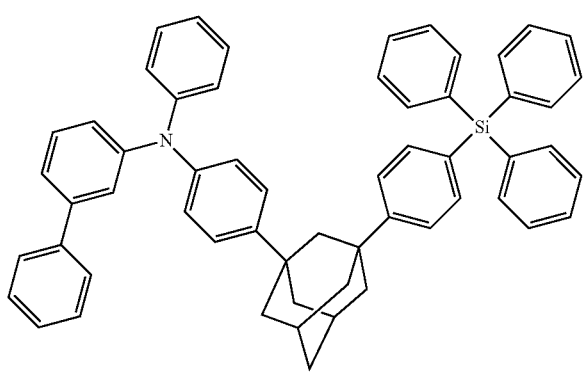

[Chemical Formula 58]

(Compound 51)

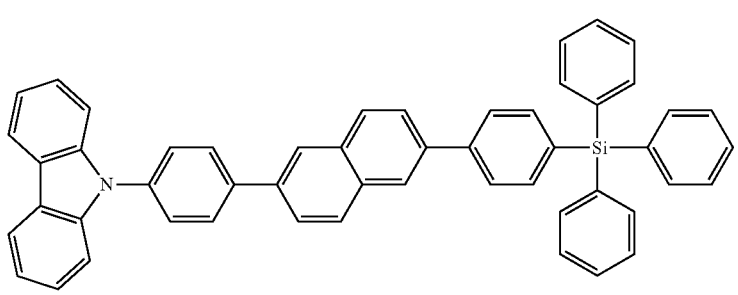

[Chemical Formula 59]

(Compound 52)

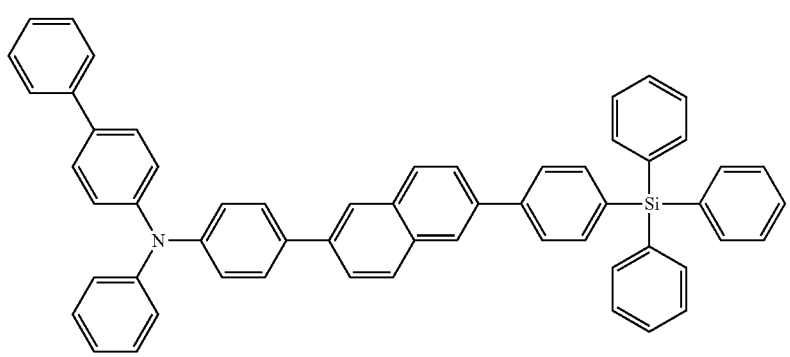

These compounds were purified using methods such as column chromatography, adsorption purification using, for example, activated carbon or activated clay, or recrystallization or crystallization with a solvent. The compounds were identified by NMR analysis. For the measurement of property values, DSC (Tg) and melting point were measured. The melting point is the index of vapor deposition property, and the glass transition point (Tg) is the index of the stability of the thin-film state.

The melting point and glass transition point were measured from a powder, using a high-sensitive differential scanning calorimeter DSC3100S (Bruker AXS).

The work function was measured from a 100-nm thin film formed on an ITO substrate, using an atmospheric photoelectron spectrometer AC-3 (Riken Keiki Co., Ltd.). The work function is the index of hole-transport and hole-blocking capabilities.

The excited triplet energy levels of the compound of the present invention can be calculated from a measured phosphorescence spectrum. The phosphorescence spectrum can be measured using a commercially available spectrophotometer. Generally, the phosphorescence spectrum may be measured by, for example, a method in which the compound is dissolved in a solvent, and irradiated with excitation light under low temperature (see, for example, Non-Patent Document 6), or a method in which the compound is vapor deposited as a thin film on a silicon substrate, and irradiated with excitation light under low temperature (see, for example, Patent Document 1). The excited triplet levels can be calculated by reading the wavelength at the first peak on the shorter wavelength side, or the wavelength at the rise on the shorter wavelength side of the phosphorescence spectrum, and then converting this value to the light energy value according to the following formula. The excited triplet levels are the index of the confinement of the triplet excitons of the phosphorescent material.

$$E(\text{eV}) = hc/\lambda \quad \text{[Formula 1]}$$

In the equation, E is the light energy value, h the Planck's constant ($6.63 \times 10^{-34}$ Js), c the speed of light ($3.00 \times 10^8$ m/s), and λ the wavelength (nm) at the rise on the shorter wavelength side of the phosphorescence spectrum. Note that 1 eV is $1.60 \times 10^{-19}$ J.

Patent Document 1: JP-A-2007-022986

Non-Patent Document 6: *Jikken Kagaku Kouza* 7, 4th Edition, p. 384-398 (1992), Ed., The Chemical Society of Japan, Maruzen An organic EL device of the present invention may be structured to include an anode, a hole injection layer, a hole transport layer, an electron blocking layer, a light emitting layer, a hole blocking layer, an electron transport layer, and a cathode, sequentially formed on a substrate. The organic EL device may further include an electron injection layer between the electron transport layer and the cathode. Some of the organic layers in this multilayer structure may be omitted. For example, the organic EL device may be structured to include an anode, a hole transport layer, a light emitting layer, an electron transport layer, and a cathode, sequentially formed on a substrate.

The light emitting layer, the hole transport layer, and the electron transport layer each may have a laminated structure of two or more layers.

Further, for example, the material commonly used for the hole injection layer and the hole transport layer may be P-doped with trisbromophenylaminium hexachloroantimonate, or a polymer compound having an N,N'-diphenyl-N,N'-di(m-tolyl)benzidine (simply "TPD") structure in its partial structure may be used for the material commonly used for these layers.

Further, the material commonly used for the electron injection layer and the electron transport layer may be N-doped with a metal such as cesium.

Electrode materials with large work functions, such as an ITO and gold, are used for the anode of the organic EL device of the present invention. The material of the hole injection layer may be, for example, copper phthalocyanine, a naphthalenediamine derivative, a starburst triphenylamine derivative, or a coating-type material. The material of the hole transport layer of the present invention may be, for example, an m-carbazolylphenyl group-containing compound, TPD, N,N'-diphenyl-N,N'-di(α-naphthyl)benzidine (simply "NPD"), or bis[N,N-di(p-tolyl)-4-aminophenyl]cyclohexane (simply "TPAC").

The compound of general formula (1) having a triphenylsilyl group and a triarylamine structure of the present invention may be used as the electron blocking layer in the organic EL device of the present invention.

The light emitting layer in the organic EL device of the present invention is fabricated by doping a hole injecting and transporting host material with a light-emitting material which is called a guest material. The compound of general formula (1) having a triphenylsilyl group and a triarylamine structure of the present invention, an electron transporting TPBI, or a triazole compound PyTAZ-02 of the following formula can be used as the host material of the light emitting layer.

[Chemical Formula 60]

(Compound 53)

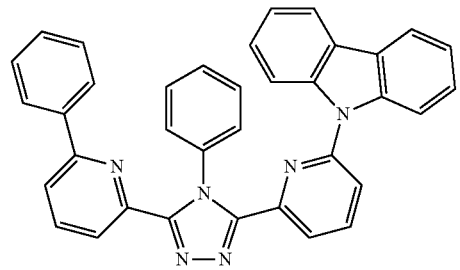

The guest material used for the light emitting layer in the organic EL device of the present invention may be a fluorescent material or a phosphorescent material. The fluorescent material may be, for example, a rubrene derivative, an anthracene derivative, or a coumalin derivative. The phosphorescent material may be, for example, a green phosphorescent material such as an iridium complex of phenylpyridine (Ir(ppy)3); a blue phosphorescent material such as FIrpic and FIr6; or a red phosphorescent material such as Btp2Ir (acac).

Because the phosphorescent guest material undergoes concentration quenching, it is preferable that 1 to 30 weight percent of the phosphorescent guest material with respect to the whole light emitting layer be doped by co-vapor deposition.

Further, a device of a structure in which a light emitting layer fabricated by using a compound of a different work function as the host material is adjacently laminated on the light emitting layer fabricated with the compound of the present invention may be fabricated (see, for example, Non-Patent Document 7).

Non-Patent Document 7: *Yuuki EL Tohronkai*, Proceeding of the First Regular Meeting, 19 (2005)

Compounds having a hole-blocking function, including phenanthroline derivatives (for example, BCP), aluminum (III) bis(2-methyl-8-quinolinate)-4-phenylphenolate (hereinafter, simply "BAlq"), oxazole derivatives, and triazole derivatives are used for the hole blocking layer in the organic EL device of the present invention.

Oxadiazole derivatives, triazole derivatives, and aluminum complexes of quinoline such as tris(8-hydroxyquinoline)aluminum (hereinafter, simply "Alq") and BAlq are used for the electron transport layer in the organic EL device of the present invention. The electron injection layer in the organic EL device of the present invention may be, for example, lithium fluoride. The electron injection layer may be omitted upon preferably selecting the electron transport layer and the cathode. Electrode materials with small work functions such as aluminum and a magnesium-silver alloy are used for the cathode in the organic EL device of the present invention.

An embodiment of the present invention is specifically described below based on Examples. The present invention, however, is not restricted to the following Examples, as long as such departures are within the scope of the invention.

EXAMPLE 1

Synthesis of 9-[4-(carbazol-9-yl)phenyl]-9-[4-(triphenylsilyl)phenyl]-9H-fluorene (Compound 25)

27.0 g of 9,9-bis(4-iodophenyl)-9H-fluorene, 8.0 g of carbazole, 1.5 g of a copper powder, 13.1 g of potassium carbonate, 0.7 ml of dimethyl sulfoxide, and 200 ml of o-dichlorobenzene were added to a reaction vessel under a nitrogen atmosphere, heated, and stirred at 160° C. for 2 hours. The mixture was allowed to cool to room temperature, heated again after adding 300 ml of toluene, and stirred at 80° C. for 1 hour. The insoluble matter was removed by filtration, and the filtrate was concentrated under reduced pressure to obtain a crude product. The crude product was then purified by column chromatography (carrier: silica gel, eluent: hexane/chloroform) to give a white powder of 9-[4-(carbazol-9-yl)phenyl]-9-(4-iodophenyl)-9H-fluorene (12.2 g; yield, 42%).

10.0 g of the 9-[4-(carbazol-9-yl)phenyl]-9-(4-iodophenyl)-9H-fluorene, and 500 ml of methyl-t-butyl ether were charged into a reaction vessel under an argon atmosphere, and cooled to −10° C. The mixture was stirred for 15 minutes after dropping 10.3 ml of n-butyllithium. Then, a solution of 9.7 g of triphenylsilyl chloride in 50 ml of dry toluene was dropped. The mixture was further stirred at −10° C. for 3 hours. After dropping an ammonium chloride aqueous solution, the mixture was stirred with addition of 300 ml of chloroform and 200 ml of water to separate an organic layer. The organic layer was dried over anhydrous magnesium sulfate, and concentrated under reduced pressure to give a crude product. The crude product was purified by column chromatography (carrier: silica gel, eluent: hexane/chloroform) to give a white powder of 9-[4-(carbazol-9-yl)phenyl]-9-[4-(triphenylsilyl)phenyl]-9H-fluorene (Compound 25; 2.5 g; yield, 21%).

The structure of the resulting white powder was identified by NMR. The result of 1H-NMR measurement is presented in FIG. 1.

1H-NMR (CDCl3) detected 39 hydrogen signals, as follows. δ (ppm)=8.10 (2H), 7.80 (2H), 7.46-7.56 (10H), 7.22-7.43 (25H).

EXAMPLE 2

The melting point and glass transition point of the compound of the present invention were determined using a high-sensitive differential scanning calorimeter (Bruker AXS, DSC3100S).

|  | Melting point | Glass transition point |
|---|---|---|
| Compound of Example 1 of the present invention | 339° C. | 142° C. |

The compound of the present invention has a glass transition point of 100° C. or more, and a stable thin-film state.

EXAMPLE 3

A 100 nm-thick vapor-deposited film was fabricated on an ITO substrate using the compound of the present invention, and the work function was measured with an atmospheric photoelectron spectrometer (Riken Keiki Co., Ltd., AC-3).

|  | Work function |
|---|---|
| Compound of Example 1 of the present invention | 5.80 eV |
| CBP | 6.00 eV |

The compound of the present invention thus has a preferable energy level compared to the CBP commonly used as the host compound of the light emitting layer.

EXAMPLE 4

A $1.0 \times 10^{-5}$ mol/L solution of 2-methyltetrahydrofuran was prepared for the compound of the present invention. The solution was charged into a designated quartz tube, and aerated with pure nitrogen to remove the oxygen. The tube was then plugged with a rubber septum to prevent entry of oxygen. After being cooled to 77K, the sample was irradiated with excitation light to measure the phosphorescence spectrum, using a spectrofluorophosphometer (Horiba Limited, FluoroMax-4). The wavelength at the rise on the shorter wavelength side of the phosphorescence spectrum was read, and the value of this wavelength was converted into light energy to calculate the excited triplet level.

|  | Excited triplet level |
|---|---|
| Compound of Example 1 of the present invention | 3.06 eV |
| CBP | 2.56 eV |
| FIrpic | 2.62 eV |

As these results show, the compound of the present invention has a value greater than triplet energy of the common blue phosphorescent material FIrpic or CBP, and is capable of sufficiently confining the excited triplet energy from the light emitting layer.

EXAMPLE 5

Figure 2:
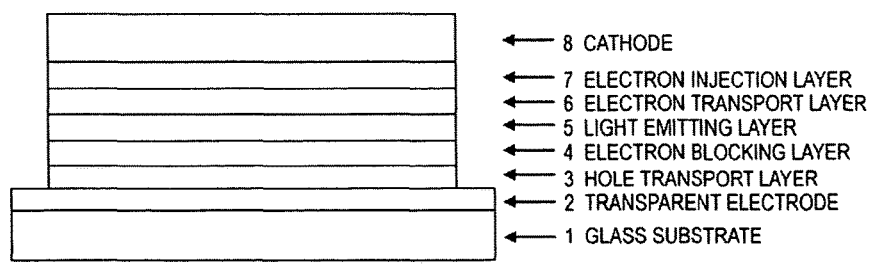
FIG. 2 is a diagram representing a configuration of EL devices of Examples 5 to 7, and Comparative Example 1.

As illustrated in FIG. 2, an organic EL device was fabricated by the vapor deposition of a hole transport layer 3, an electron blocking layer 4, a light emitting layer 5, an electron transport layer 6, an electron injection layer 7, and a cathode (aluminum electrode) 8 deposited in this order on an ITO electrode formed in advance as a transparent electrode 2 on a glass substrate 1. The glass substrate 1 with ITO formed in a film thickness of 150 nm was washed with an organic solvent, and the surface was further washed by an oxygen plasma process. The glass substrate with the ITO electrode was then installed in a vacuum vapor deposition apparatus, and the pressure was reduced to 0.001 Pa or less.

Thereafter, an NPD having a thickness of 40 nm was formed as the hole transport layer 3 at a deposition rate of 1.0 Å/sec so as to cover the transparent electrode 2. The compound of Example 1 of the present invention (Compound 25) was then formed as the electron blocking layer 4 on the hole transport layer 3 at a deposition rate of 1.0 Å/sec and in a thickness of 10 nm. The triazole compound PyTAZ-02 (Compound 41) and the blue phosphorescent material FIrpic were then formed as the light emitting layer 5 on the electron blocking layer 4 in a thickness of 20 nm by the dual vapor deposition performed at the PyTAZ-02 (Compound 41):FIrpic deposition rate ratio of 94:6. Thereafter, Alq was formed as the electron transport layer 6 on the light emitting layer 5 at a deposition rate of 1.0 Å/sec and in a thickness of 45 nm. Then, lithium fluoride was formed as the electron injection layer 7 on the electron transport layer 6 at a deposition rate of 0.1 Å/sec and in a thickness of 0.5 nm. Finally, aluminum was vapor deposited in a thickness of 150 nm to form the cathode 8. The characteristics of the organic EL device fabricated as above were then measured in an atmosphere at ordinary temperature.

Table 1 below presents the measurement results of emission characteristics obtained in response to the applied DC voltage to the organic EL device fabricated with the compound of Example 1 of the present invention (Compound 25).

The external quantum efficiency under a current flown at a current density of 100 mA/cm$^2$ was 3.0%.

The external quantum efficiency under a current flown at a current density of 2.0 mA/cm$^2$ was 14.7%.

Comparative Example 1

For comparison, an organic EL device was fabricated under the same conditions of Example 5, except that CBP was used as the material of the electron blocking layer 4. The characteristics of the organic EL device were measured in an atmosphere at ordinary temperature.

Table 1 below presents the measurement results of emission characteristics obtained in response to the applied DC voltage to the organic EL device.

TABLE 1

| | Compound | Voltage [V] (@1,000 cd/m$^2$) | Current density [mA/cm$^2$] (@1,000 cd/m$^2$) | Luminous efficiency [cd/A] (@1,000 cd/m$^2$) | Power Efficiency [lm/W] (@1,000 cd/m$^2$) |
|---|---|---|---|---|---|
| Ex. 5 | Compound 25 | 7.53 | 3.11 | 32.15 | 13.38 |
| Com. Ex. 1 | CBP | 7.31 | 9.22 | 10.85 | 4.66 |

As presented in Table 1, the current density at the 1,000 cd/m$^2$ luminance reduces to about ⅓, and the luminous efficiency and power efficiency show about a 3-fold increase with the use of the compound of Example 1 of the present invention (Compound 25) as the material of the electron blocking layer.

EXAMPLE 6

An organic EL device was fabricated in the same manner as in Example 5, except that the light emitting layer 5 was formed as follows. A 10 nm-thick thin film of the compound of Example 1 of the present invention (Compound 25) and the blue phosphorescent material FIrpic was formed on the electron blocking layer 4 by the dual vapor deposition performed at the deposition rate ratio of the compound of Example 1 of the present invention (Compound 25) and FIrpic of 94:6. A 10 nm-thick thin film of the triazole compound PyTAZ-02 (Compound 41) and the blue phosphorescent material FIrpic was then formed on the thin film of Compound 25 and FIrpic by the dual vapor deposition performed at the deposition rate ratio of the PyTAZ-02 (compound 41) and FIrpic of 94:6. The characteristics of the organic EL device were measured in an atmosphere at ordinary temperature. The external quantum efficiency under a current flown at a current density of 100 mA/cm$^2$ was 4.0%.

Specifically, the external quantum efficiency at the current density of 100 mA/cm$^2$ improved with the bilayer structure of the light emitting layer in which the compound of Example 1 of the present invention (Compound 25) was used as the host compound in one of these light emitting layers.

EXAMPLE 7

An organic EL device was fabricated in the same manner as in Example 5, except that the TPBI was formed as the electron transport layer 6 at a deposition rate of 1.0 Å/sec and in a thickness of 45 nm. The characteristics of the organic EL device were measured in an atmosphere at ordinary temperature. The external quantum efficiency under a current flown at a current density of 2.0 mA/cm$^2$ was 18.2%.

Specifically, because of the superior electron blocking capability of the compound of Example 1 of the present invention (Compound 25), the use of TPBI as the compound for the electron transport layer further improved the external quantum efficiency at a current density of 2.0 mA/cm$^2$.

It can be said from these results that the compound of the present invention, with its high excited triplet levels and the ability to desirably transfer energy to the phosphorescent material and completely confine the triplet excitons of the phosphorescent material, has excellent characteristics as the host compound of the light emitting layer and as the electron-blocking compound.

INDUSTRIAL APPLICABILITY

The compound having a triphenylsilyl group and a triarylamine structure of the present invention has high excited triplet levels, and can completely confine the triplet excitons of the phosphorescent material. The compound therefore has excellent characteristics as the host compound of alight emitting layer and as an electron-blocking compound. Further, use of the compound for the fabrication of an organic EL device can greatly improve the luminance and the luminous efficiency of the organic EL device, and thus can improve the performance of mobile electronic products.

DESCRIPTION OF REFERENCE NUMERALS AND SIGNS

1 Glass substrate
2 Transparent electrode
3 Hole transport layer
4 Electron blocking layer
5 Light emitting layer 6 Electron transport layer
7 Electron injection layer
8 Cathode

The invention claimed is:
1. A compound of the general formula (1) below having a triphenylsilyl group and a triarylamine structure,

[Chemical Formula 1]

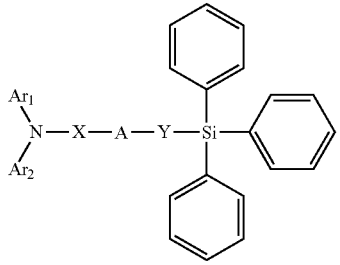

(1)

(wherein X and Y may be the same or different, and represent a substituted or unsubstituted divalent aromatic hydrocarbon group, wherein the substituted or unsubstituted divalent aromatic hydrocarbon group includes divalent groups that result from the removal of two hydrogen atoms from compounds benzene, naphthalene, and anthracene, Ar1 and Ar2 may be the same or different, and represent a substituted or unsubstituted aromatic hydrocarbon group, a substituted or unsubstituted aromatic heterocyclic group, or a substituted or unsubstituted condensed polycyclic aromatic group, which may bind to each other to form a ring structure, and A represents a divalent group of the structural formulae (E) below)

[Chemical Formula 5]

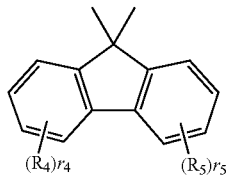

(E)

(wherein R4 and R5 may be the same or different, and represent a fluorine atom, a chlorine atom, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group, where a plurality of R4 or R5 may be different from each other, r4 and r5 are integers of 0 to 4, where the divalent group (E) is not substituted with R4 or R5 when r4 or r5 is 0).

2. An organic electroluminescent device that comprises a pair of electrodes, and at least one organic layer interposed between the pair of electrodes, wherein a compound of the general formula (1) below having a triphenylsilyl group and a triarylamine structure is used as constituent material of the at least one organic layer,

[Chemical Formula 10]

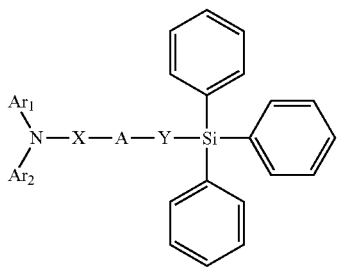

(1)

(wherein X and Y may be the same or different, and represent a substituted or unsubstituted divalent aromatic hydrocarbon group, wherein the substituted or unsubstituted divalent aromatic hydrocarbon group includes divalent groups that result from the removal of two hydrogen atoms from compounds benzene, naphthalene, and anthracene, Ar1 and Ar2 may be the same or different, and represent a substituted or unsubstituted aromatic hydrocarbon group, a substituted or unsubstituted aromatic heterocyclic group, or a substituted or unsubstituted condensed polycyclic aromatic group, which may bind to each other to form a ring structure, and A represents a divalent group of the structural formulae (E) below)

[Chemical Formula 14]

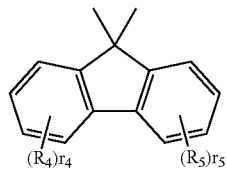

(E)

(wherein R4 and R5 may be the same or different, and represent a fluorine atom, a chlorine atom, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group, where a plurality of R4 or R5 may be different from each other, r4 and r5 are integers of 0 to 4, where the divalent group (E) is not substituted with R4 or R5 when r4 or r5 is 0).

3. An organic electroluminescent device of claim 2, wherein the organic layer is an electron blocking layer, and wherein the compound of the general formula (1) is used as at least one constituent material in the electron blocking layer.

4. An organic electroluminescent device of claim 2, wherein the organic layer is a light emitting layer, and wherein the compound of the general formula (1) is used as at least one constituent material in the light emitting layer.

5. An organic electroluminescent device of claim 2, wherein the organic electroluminescent device is a sequential laminate of at least two kinds of light emitting layers, and wherein the compound of the general formula (1) is used as at least one constituent material in one of the light emitting layers.

6. An organic electroluminescent device of claim 4, wherein the organic electroluminescent device is a sequential laminate of at least two kinds of light emitting layers, and wherein the compound of the general formula (1) is used as at least one constituent material in one of the light emitting layers.

7. A compound having a triphenylsilyl group and a triarylamine structure of claim 1, wherein X and Y represent an unsubstituted divalent aromatic hydrocarbon group that results from the removal of two hydrogen atoms from benzene.

8. An organic electroluminescent device of claim 2, wherein X and Y represent an unsubstituted divalent aromatic hydrocarbon group that results from the removal of two hydrogen atoms from benzene.

9. A compound of the general formula (1) below having a triphenylsilyl group and a triarylamine structure,

[Chemical Formula 19]

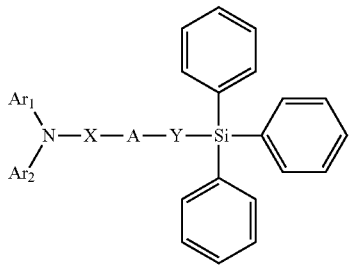

(1)

(wherein X and Y may be the same or different, and represent a substituted or unsubstituted divalent aromatic hydrocarbon group, Ar1 and Ar2 may be the same or different, and represent a substituted or unsubstituted aromatic hydrocarbon group, a substituted or unsubstituted aromatic heterocyclic group, or a substituted or unsubstituted condensed polycyclic aromatic group, which bind to each other to form a ring structure, and A represents a divalent group of the structural formulae (E) below or a single bond)

[Chemical Formula 23]

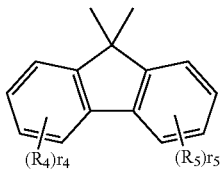

(E)

(wherein R4 and R5 may be the same or different, and represent a fluorine atom, a chlorine atom, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group, where a plurality of R4 or R5 may be different from each other, r4 and r5 are integers of 0 to 4, where the divalent group (E) is not substituted with R4 or R5 when r4 or r5 is 0).

* * * * *